United States Patent [19]

Lee

[11] Patent Number: 4,752,418
[45] Date of Patent: Jun. 21, 1988

[54] PARAFFIN SULFONATE PROCESS
[75] Inventor: John Y. Lee, Baton Rouge, La.
[73] Assignee: Ethyl Corporation, Richmond, Va.
[21] Appl. No.: 791,052
[22] Filed: Oct. 24, 1985
[51] Int. Cl.⁴ .............................................. C07C 143/02
[52] U.S. Cl. ................................................. 260/513 R
[58] Field of Search ................................... 260/513 R

[56] References Cited
U.S. PATENT DOCUMENTS
3,329,708  7/1967  Berger ............................ 260/513 R OTHER PUBLICATIONS
Wallace et al., J. Org. Chem. 27, 1514–16 (1962).
Wallace et al., Tetrahedron 21, 2271–80 (1965).
Wallace et al., J. Appl. Chem. 17, 48–52 (1967).
Wallace et al., J. Inst. Petro. 53, 207–214 (1967).

*Primary Examiner*—Alan Siegel
*Attorney, Agent, or Firm*—J. F. Sieberth; J. D. Odenweller

[57] ABSTRACT

Alkyl mercaptans, especially sec-alkyl mercaptans, are oxidized to paraffin sulfonates by reaction with oxygen in a tert-alkanol solvent in the presence of a stoichiometric deficiency of base such as alkali hydroxide or alkoxide or tetraalkyl ammonium hydroxide. Yield of paraffin sulfonate salt is almost quantitative. By-product dialkyl disulfide can be recycled.

20 Claims, No Drawings

PARAFFIN SULFONATE PROCESS

BACKGROUND OF THE INVENTION

Salts of alkyl sulfonic acids are used as detergents especially in dishwashing formulations. These detergents are generally referred to as paraffin sulfonates. They can be made from so called detergent range olefins by reacting the olefin with hydrogen sulfide to form an alkyl mercaptan and then oxidizing the mercaptan to a sulfonic acid. It has been reported that this oxidation can be conducted using oxidizing agents such as nitric acid, hydrogen peroxide, chlorine plus oxygen and by oxygen in the presence of base. The present invention is concerned with this later process.

Wallace and Schriesheim have published a number of papers on their work on the base catalyzed oxidation of mercaptans. In J. Org. Chem. 27, 1514 (1962) they report the oxidation of n-butyl mercaptan at 23.5° C. in methanol, tetrahydrofuran, dioxane, diglyme, dimethylacetamide, dimethylformamide, ethanol and tert-butyl alcohol. They used 2 moles of base per mole of mercaptan. The products made were disulfides, not sulfonates.

In Tetrahedron 21, 2271 (1965), Wallace et al. report the formation of sulfonic acids by increasing the amount of base to 4 moles per mole of mercaptan. Solvents used were hexamethylphosphoramide, dimethylformamide, tetramethylurea and pyridine. In methanol at a 2:1 base:mercaptan ratio only disulfides formed.

Wallace et al., J. Appl. Chem. 17, 48 (1967) report continued research using hexamethylphosphoramide, their preferred solvent, dimethylformamide, tetramethylurea, pyridine and methanol. Using methanol at 4 moles of base per mole of mercaptan only disulfides formed.

In J. Inst. Petro. 53, No. 522, 207 (1967), Wallace et al. report their research on the oxidation of mercaptans in petroleum fractions with air and an aqueous base. Normally this process is only effective up to $C_5$ mercaptans due to the lack of solubility of the higher mercaptans in aqueous base. Solubilizers that have been used are methanol, amino alcohols, glycols, polyglycols and surfactants. Wallace et al. directed their efforts at the effect of methanol, tert-butyl alcohol, dimethoxyethane, dimethyl sulfoxide, dimethylformamide and hexamethylphosphoramide as co-solvents and found hexamethylphosphoramide to be superior. The oxidation products are disulfides. They also speculate that the mercaptide ion is the active species that is oxidized to disulfide which is why an excess of base was required.

SUMMARY OF THE INVENTION

It has now been discovered that alkyl mercaptans can be oxidized to sulfonic acids by contact with oxygen in a lower alkanol which contains far less than the stoichiometric amount of base. Under these base deficient conditions, yields of sulfonic acid salt is almost quantititative based on the amount of base present to form salt. The sulfonic acid formed neutralizes the base. Despite this apparent lack of the required mercaptide anions as the oxidation proceeds, the rest of the mercaptan is oxidized to disulfides. Furthermore, under these base deficient conditions, formation of carboxylic acid by-product is decreased.

DESCRIPTION OF THE PREFERRED EMBODIMENTS

A preferred embodiment of the invention is a process for oxidizing an alkyl mercaptan to form a paraffin sulfonate, said process comprising
(a) forming a mixture of 0.1–0.9 mole parts of a base selected from alkali metal hydroxides, alkoxides and tetraalkyl ammonium hydroxides with 1 mole part of an alkyl mercaptan or mixtures thereof containing about 8–20 carbon atoms in a lower alkanol solvent,
(b) contacting the alkanol solution with an oxygen-containing gas while maintaining the temperature of the mixture in the range of about 60°–120° C. to form a salt of a paraffin sulfonic acid.

The process is very effective on alkyl mercaptans which contain about 8–20 carbon atoms such as octyl mercaptan, 2-ethylhexyl mercaptan, decyl mercaptan, 2-ethyldecyl mercaptan, dodecyl mercaptan, 2-mercapto hexane, 3-mercapto hexane, 2-mercapto octane, 4-mercapto decane, 4-mercapto-2-ethyl decane, 7-mercapto tetradecane, 4-mercapto hexadecane, 6-mercapto octadecane, 9-mercapto eicosane and the like.

The products are especially useful when the alkyl mercaptan feed stock is a sec-alkyl mercaptan or a mixture containing a major amount of sec-alkyl mercaptans. For example, mercaptan mixtures that are at least 80 mole percent sec-alkyl mercaptans formed paraffin sulfonate salts that are very effective in liquid dishwashing detergent. The sec-alkyl mercaptans are especially useful when the alkyl groups contain about 12–18 carbon atoms.

The base catalyst can be any alkali metal hydroxide or alkoxide such as sodium hydroxide, potassium hydroxide, lithium hydroxide, sodium tert-butoxide, potassium tert-pentoxide and the like. Also tetraalkyl ammonium hydroxide is a useful base for use in the present process. Examples of these are tetramethyl ammonium hydroxide, tetrabutyl ammonium hydroxide, tetraoctyl ammonium hydroxide, dimethyl dibutyl ammonium hydroxide, and the like.

Useful alkanols include the lower alkanols containing up to about 12 carbon atoms. Examples of these are methanol, ethanol, n-propanol, isopropanol, n-butanol, isobutanol, secbutanol, tert-butanol, isopentanol, n-hexanol, 2-ethylhexanol and the like. More preferably the lower alkanols will contain about 1–6 carbon atoms.

The preferred alkanols are the lower tert-alkanols. Useful tert-alkanol solvents include those which contain from 4 to about 12 carbon atoms such as tert-butanol, 2-methyl-2-pentanol, 2-ethyl-2-pentanol, 3-methyl-3-hexanol, 3,7-dimethyl-3-octanol, 5-methyl-5-nonanol, 5-methyl-5-decanol, 3-methyl-3-undecanol and the like. The preferred tert-alkanol is tertbutanol.

The amount of alkanol is a solvent amount. This can range from about 1 up to about 10 or more parts by weight per each part of alkyl mercaptan. A preferred range is about 2–5 parts of alcohol per part of alkyl mercaptan.

It is important to limit the amount of base substantially below the amount which would be stoichiometrically equivalent to the amount of mercaptan. Preferably the amount of base should be in the range of 0.1–0.9 moles per mole of alkyl mercaptan. More preferably the amount of base is in the range of 0.1–0.8 moles per mole of alkyl mercaptan. Still more preferably the base is in the range of only 0.1–0.5 moles per mole of alkyl mercaptan.

Although the reaction system need not be anhydrous, the use of wet reactants is preferably avoided. The water normally present in commercial alkanols and alkaline bases is not detrimental.

The reaction is conducted at a temperature high enough to cause the oxidation to proceed to form the paraffin sulfonate salt but not so high as to cause degradation of the solvent or products. A useful temperature range is from ambient (e.g. 20° C.) up to reflux or higher under pressure. A more preferred range is about 75°–120° C. With the lower tert-alkanol this will require moderate pressures since for example tert-butanol boils at about 82° C. under atmospheric pressure. Since the reaction is usually conducted under oxygen or air pressure, the pressure requirement to reach the higher temperatures is easily satisfied.

Either oxygen or air can be used as the oxygen source. The amount of oxygen should be an amount at least equivalent to the moles of base. Preferably an excess amount of oxygen is used up to about 10 or more times the amount theoretically required to oxidize the alkyl mercaptan to a sulfonic acid. This stoichiometry requires 1.5 moles of oxygen per mole of alkyl mercaptan.

The oxygen-containing gas may be merely bubbled through the tert-alkanol solvent or it may be passed into the tert-alkanol under pressure. Hence the oxidation can be conducted at pressures ranging from atmospheric up to 500 psig or higher if desired. When using an impure oxygen source such as air and operating in a closed system under pressure the vapor space should be continuously or periodically purged to prevent a buildup of inert gas such as nitrogen. With oxygen there is no need to purge and the system can be merely pressurized to the desired reaction pressure with oxygen and additional oxygen introduced as required to maintain the desired pressure.

The oxidation rate is improved by conducting the reaction with vigorous agitation to assist in transfer of oxygen into the liquid phase.

The oxidation is usually complete in less than 8 hours. A useful reaction time is about 0.5–12 hours. A more preferred reaction time is about 1–8 hours and good yields of paraffin sulfonate salts are usually achieved in about 2–6 hours.

The amount of sulfonate salt formed is nearly quantitative based on the base. Thus if 1 mole of sodium hydroxide is added to tert-alkanol containing 4 moles of alkyl mercaptan, the product would contain close to 1 mole of sodium alkyl sulfonate. The remaining alkyl mercaptan will oxidize to form dialkyl disulfide which is entirely unexpected in view of the teaching of Wallace et al. that the mercaptide ion is the active specie. When using a stoichiometric deficiency of base, the base is consumed by the sulfonic acid so that as the later part of the reaction, there isn't any base to form mercaptide ion. Despite this and the teaching of Wallace et al. that a large excess of base is needed, the present reaction system oxidizes all of the remaining alkyl mercaptan to dialkyl disulfide during formation of an amount of paraffin sulfonate salt equal to the amount of base present in the system.

The paraffin sulfonate salt can be separated from the reaction mixture by adding water. The sulfonate salts are water soluble and will extract into the aqueous phase and can be separated. This can be first purified by extraction with a low boiling aliphatic hydrocarbon such as pentane to remove any non-sulfonic products referred to collectively as "free-oil". The aqueous phase can then be acidified to regenerate the paraffin sulfonic acid.

The non-water soluble coproduct is mainly dialkyl disulfide. This can be chemically reduced back to alkyl mercaptan and reused in the process. Preferably the dialkyl disulfide is recycled to the next reaction cycle where it is used to replace part of the alkyl mercaptan normally charged on the basis of each mole of dialkyl disulfide replacing 2 moles of alkyl mercaptan. Other than this, the recycle runs are conducted in the same manner as the initial run. The following examples serve to show how the process can be carried out.

EXAMPLE 1

In a reaction vessel was placed 460 grams tert-butanol, 230 grams (1 mole) 7-mercapto-tetradecane and 11.73 grams 98% NaOH (0.288 mole). The vessel was sealed and, while stirring, heated to 95° C. under 100 psig oxygen pressure. Stirring was continued 10 hours under these conditions. The reaction mixture was then cooled and degassed. Tert-butanol solvent was stripped off under reduced pressure. Dilute, cold HCl was added to acidify the residue, which was then extracted (3×20 ml portion) by diethyl ether. The ether solution was dried over $Na_2SO_4$ and then distilled to give 276 grams crude product mixture. GC analysis showed no residual 7-mercapto-tetradecane (100% conversion). The IR spectrum showed that the functional group of the secondary paraffin sulfonate (which is identical to that of a known commercial secondary paraffin sulfonate sample). Proton NMR data (with 1,1,2,2-tetrachloroethane as internal standard) showed the yields (based on 7-mercapto-tetradecane charged): di-7-tetradecyl disulfide, 68%; 7-tetradecyl sulfonate, 26% carboxylic acid, 2%; and unknown intermediate, 3–4%. Based on the NaOH used, the yield of the desired product was 90%.

EXAMPLE 2

In a reaction vessel was placed 377 grams tert-butanol, 230 grams (1 mole) 7-mercapto-tetradecane and 14.45 grams 98% NaOH (0.354 mole). The vessel was sealed and, while stirring, heated to 80° C. under 100 psig oxygen pressure. Stirring was continued 6 hours under these conditions. The reaction mixture was cooled and then degassed. After the same workup and analysis as in Example 1, the results were: di-7-tetradecyl disulfide, 77%; 7-tetradecyl sulfonate, 21%; and carboxylic acid, 1–2%. Based on the NaOH used (35.4%), the yield of the desired product was 62%.

EXAMPLE 3

In a reaction vessel was placed 460 grams tert-butanol, 230 grams (1 mole) 7-mercapto-tetradecane and 7.51 grams 98% NaOH (0.184 mole). The vessel was sealed and, while stirring, heated to 80° C. under 100 psig oxygen pressure. Stirring was continued 5 hours under these conditions and then the reaction mixture was cooled and degassed. After the same workup and analysis as in Example 1, the results were: di-7-tetradecyl disulfide, 72%; 7-tetradecyl sulfonate, 19%; carboxylic acid, 1%; and unknown intermediate, 5%. Based on the NaOH used (18.4%), the yield of sulfonate was essentially quantitative.

As the third example shows, the process using a deficiency of base gives almost a quantitative yield of alkane sulfonic acid based on NaOH and converts the remainder of the alkyl mercaptan to dialkyl disulfide which can be reduced to alkyl mercaptan or recycled directly to a subsequent oxidation under substantially the same conditions to replace a portion of the alkyl mercaptan.

I claim:

1. A process for oxidizing an alkyl mercaptan to form a paraffin sulfonate, said process comprising
   (a) forming a mixture of 0.1–0.5 mole parts of a base selected from alkali metal hydroxides, alkoxides and tetraalkyl ammonium hydroxides with 1 mole part of an alkyl mercaptan or mixtures thereof containing about 8–20 carbon atoms in a lower alkanol solvent,
   (b) contacting the alkanol solution with an oxygen-containing gas while maintaining the temperature of the mixture in the range of about 75°–120° C. to form a salt of a paraffin sulfonic acid thereby converting said alkyl mercaptan to said paraffin sulfonic acid salt in high yield calculated on the amount of base used.

2. A process of claim 1 wherein said alkanol is a tert-alkanol.

3. A process of claim 2 wherein said alkyl mercaptan or mixture thereof contains about 12–18 carbon atoms.

4. A process of claim 2 wherein said alkyl mercaptan or mixture thereof is at least 80 mole percent sec-alkyl mercaptan.

5. A process of claim 4 wherein said alkyl mercaptan is at least 90 mole percent sec-alkyl mercaptan.

6. A process of claim 2 wherein said base is an alkali metal hydroxide.

7. A process of claim 6 wherein said alkali metal hydroxide is sodium hydroxide.

8. A process of claim 7 wherein about 0.15–0.4 mole parts of sodium hydroxide are used per mole part of said alkyl mercaptan.

9. A process of claim 8 wherein at least 80 mole percent of said alkyl mercaptan is a sec-alkyl mercaptan or mixtures thereof.

10. A process of claim 9 conducted at a temperature of about 80°–100° C.

11. A process of claim 2 wherein said oxygen-containing gas is oxygen.

12. A process of claim 10 wherein said oxygen-containing gas is oxygen.

13. A process of claim 12 conducted under an oxygen pressure of about 50–200 psig.

14. A process of claim 1 including the steps of recovering paraffin sulfonate from the reaction mixture leaving dialkyl disulfide by-product and recycling said by-product to a subsequent cycle carried out in substantially the same manner whereby said recycled by-product replaces part of the initial 1 mole part of alkyl mercaptan on the basis of each mole part of dialkyl disulfide replacing 2 mole parts of alkyl mercaptan.

15. A process of claim 14 wherein said alkanol is a tert-alkanol.

16. A process of claim 15 wherein said base is an alkali metal hydroxide.

17. A process of claim 16 wherein said alkali metal hydroxide is sodium hydroxide.

18. A process of claim 17 wherein said alkyl mercaptans are at least 80 mole percent sec-alkyl mercaptans or mixtures thereof 19. A process of claim 18 conducted in the range of about 80°–100° C.

20. A process of claim 18 wherein said alkyl mercaptan contains about 12–18 carbon atoms.

* * * * *